(12) United States Patent
Hughes et al.

(10) Patent No.: US 8,334,366 B1
(45) Date of Patent: Dec. 18, 2012

(54) MUTANT LYCOTOXIN-1 PEPTIDE SEQUENCES FOR INSECTICIDAL AND CELL MEMBRANE ALTERING PROPERTIES

(75) Inventors: Stephen R. Hughes, Peoria, IL (US); Patrick F. Dowd, Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 293 days.

(21) Appl. No.: 12/770,343

(22) Filed: Apr. 29, 2010

Related U.S. Application Data

(60) Provisional application No. 61/214,835, filed on Apr. 29, 2009.

(51) Int. Cl.
*C07K 14/00* (2006.01)
*C07H 21/02* (2006.01)
*C12N 15/00* (2006.01)
(52) U.S. Cl. .................. 530/350; 536/23.1; 435/320.1
(58) Field of Classification Search .................. 530/350; 536/23.1; 435/320.1
See application file for complete search history.

(56) References Cited

OTHER PUBLICATIONS

Hughes, Stephen R., et al., "High-throughput screening of cellulase F mutants from multiplexed plasmid sets using an automated plate assay on a functional proteomic robotic workcell", Proteome Science, 2006, 4:10.

Hughes, Stephen R., et al., "Cost-Effective High-Throughput Fully Automated Construction of a Multiplex Library of Mutagenized Open Reading Frames for an Insecticidal Peptide Using a Plasmid-Based Functional Proteomic Robotic Workcell with Improved Vacuum System", JALA, Aug. 2007, 12, pp. 202-212.

Hughes, Stephen R., et al., "Lycotoxin-1 insecticidal peptide optimized by amino acid scanning mutagenesis and expressed as a coproduct in an ethanologenic *Saccharomyces cerevisiae* strain", Journal of Peptide Science, online publication May 1, 2008.

*Primary Examiner* — Karen Cochrane Carlson
(74) *Attorney, Agent, or Firm* — John Fado; Randall E. Deck; Lesley Shaw

(57) ABSTRACT

Lycotoxin-1 peptide mutant peptides which exhibit increased insecticidal activity are produced by substitution of both a proline for the lysine at amino acid position 24 and a tryptophan for the leucine at amino acid position 25 of the wild-type amino acid sequence for lycotoxin-1. Further substitution of amino acids 8, 9 or 10 of the lycotoxin-1 wild-type amino acid sequence, specifically substituting a histidine for the phenylalanine at amino acid position 8, a glutamine for the glycine at amino acid position 10, or a serine for the leucine at amino acid position 9, provides an even greater increase in insecticidal activity. In addition to changes in the lycotoxin-1 amino acid sequence, the addition of an enterokinase K recognition site, DDDK, to the N-terminus of the lycotoxin-1 peptide increases insecticidal activity further still. Isolated nucleic acid sequences encoding the mutant lycotoxin-1 peptides, expression vectors containing these sequences, microorganisms or other host cells transformed with these vectors, and recombinant methods for producing the peptides, are also disclosed.

19 Claims, 1 Drawing Sheet

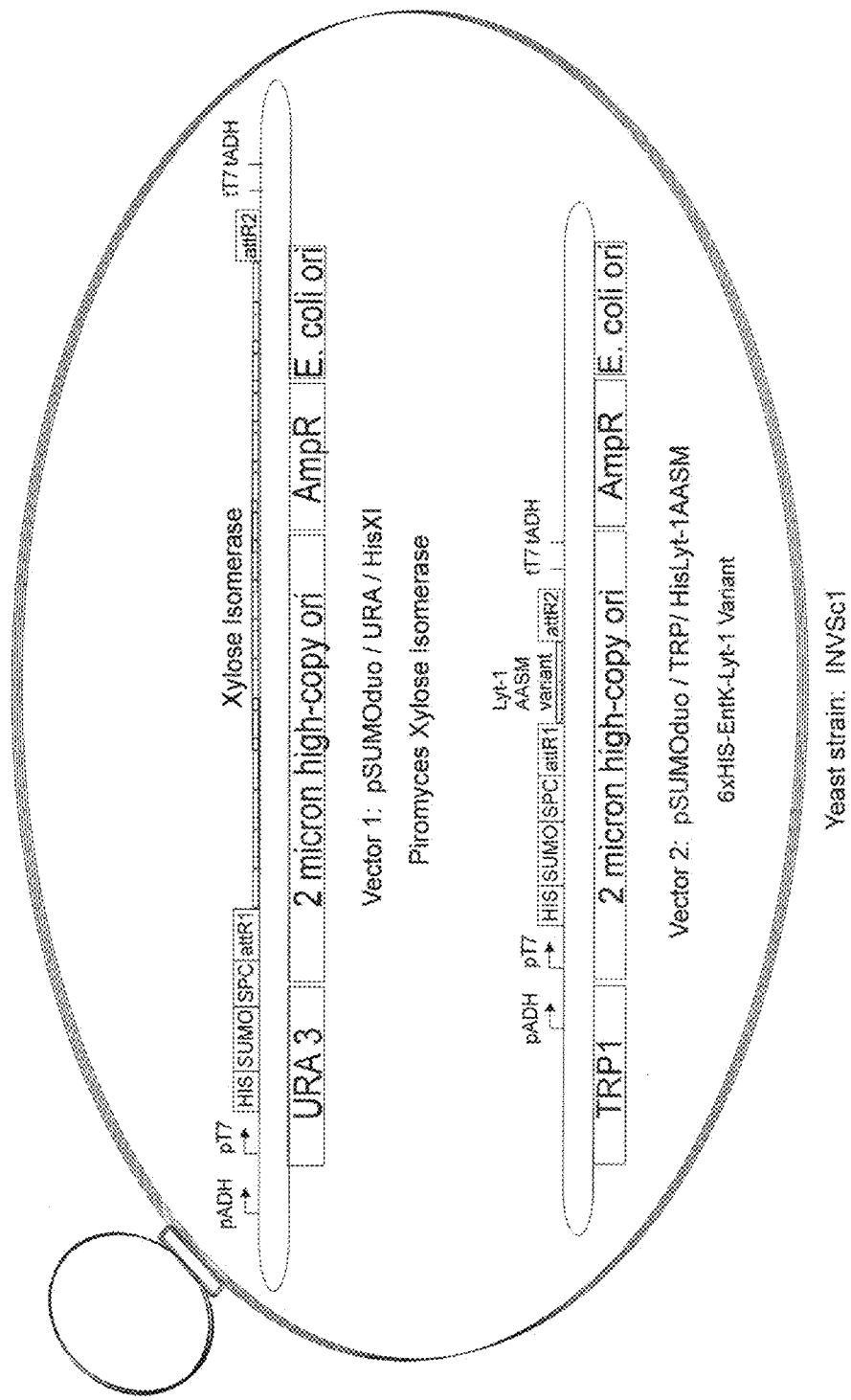

US 8,334,366 B1

MUTANT LYCOTOXIN-1 PEPTIDE SEQUENCES FOR INSECTICIDAL AND CELL MEMBRANE ALTERING PROPERTIES

CROSS REFERENCE TO RELATED APPLICATION

This application claims the benefit under 35 U.S.C. 1.19(e) of U.S. provisional No. 61/214,835, filed Apr. 29, 2009, the contents of which are incorporated by reference herein.

BACKGROUND OF THE INVENTION

1. Field of the Invention

The invention relates to recombinant mutants of the peptide lycotoxin-1, and the use of these peptides for insect and microbial control, transmembrane carrier tags, and expression level enhancer tags.

2. Description of the Prior Art

It is estimated that insect pests destroy 20-30% of the world's crop production [Oerke. In *Crop Production and Crop Protection—Estimated Losses in Major Food and Cash Crops*, Oerke et al. (eds). Elsevier: Amsterdam; 1994]. In many cases, natural enemies are not sufficient to control pests adequately [Hopper. United States department of agriculture—Agricultural Research Service research on biological control of arthropods. *Pest Manag. Sci.* 2003; 59(6-7): 643-653]. The *Bacillus thuringiensis* (Bt) crystal protein is one example of an insecticidal protein that has been developed commercially. It is highly effective against a targeted range of species depending on the clone [Hussein et al. Beetle-specific *Bacillus thuringiensis* Cry3Aa toxin reduces larval growth and curbs reproduction in *Spodoptera littoralis* (Boisd.). *Pest Manag. Sci.* 2005; 61: 1186-1192. and Herrero et al. *Bacillus thuringiensis* CryICa-resistant *Spodoptera exigua* lacks expression of one of four aminopeptidase N genes. *BMC Genomics* 2005; 6: 96] and has been employed in plants through transgenic production [Lambert et al. A *Bacillus thuringiensis* insecticidal crystal protein with a high activity against members of the family Noctuidae. *Appl. Environ. Microbiol.* 1996; 62(1): 80-86. Buntin et al. Plant-incorporated *Bacillus thuringiensis* resistance for control of fall armyworm and corn earworm (Lepidoptera: Noctuidae) in corn. *J. Econ. Entomol.* 2004; 97(5): 1603-1611. and Dowd et al. Strategies for insect management targeted toward mycotoxin management. In *Aflatoxin and Food Safety*, Abbas (ed.). Marcel Dekker: New York, 2005; 517-541] for complete control of some insect species, such as European corn borers [Peairs. 2002, 2003, 2006, 2007; (last update Sep. 24, 2007). Managing corn pests with Bt corn. Colorado State University Extension Bulletin No. 0.708, www.ext.colostate.edu/Pubs/crops/00708.html]. With commercialization of transgenic crops expressing Bt toxins, selection pressure has increased and there is concern that target insects may develop resistance to individual Bt proteins, requiring structured refuges of non-Bt host plants where Bt hybrids are grown [Peairs, ibid]. Even with such resistance management strategies, there is still concern that resistance will develop in insect pests receiving sublethal doses [Siegfried et al. Baseline susceptibility of western corn rootworm (Coleoptera: Crysomelidae) to Cry3Bb1 *Bacillus thuringiensis* toxin. *J. Econ. Entomol.* 2005; 98(4): 1320-1324], and cross-resistance to different Bt proteins has been reported [Ferŕe and Van Rie. Biochemistry and genetics of insect resistance to *Bacillus thuringiensis*. *Annu. Rev. Entomol.* 2002; 47: 501-533]. Combinations of insecticidal protein genes may be needed for more durable control [Walker et al. A QTL that enhances and broadens Bt insect resistance in soybean. *Theor. Appl. Genet.* 2004; 109: 1051-1057]. Both synthetic materials [Nauen R, Smagghe G. Mode of action of etoxazole. *Pest Manag. Sci.* 2006; 62: 379-382] and naturally derived plant extracts [Céspedes et al. Insect growth regulatory effects of some extracts and sterols from *Myrtillocactus geometrizans* (Cactaceae) against *Spodoptera frugiperda* and *Tenebrio molitor. Phytochemistry* 2005; 66: 2481-2493] continue to be explored as alternatives to Bt proteins.

The peptides in spider venoms appear to have potential for insect control owing to their specificity for the insect nervous system [Tedford et al. Scanning mutagenesis of omega-atracotoxin-Hv1a reveals a spatially restricted epitope that confers selective activity against insect calcium channels. *J. Biol. Chem.* 2004; 279(42): 44133-44140. and Wang et al. Discovery and structure of a potent and highly specific blocker of insect calcium channels. *J. Biol. Chem.* 2001; 276(43): 40306-40312]. Toxins from spider venoms define new insecticide targets owing to specific action to block insect voltage-gated $Ca^{2+}$ channels [Nicholson and Graudins. Spiders of medical importance in the Asia-Pacific: atracotoxin, latrotoxin and related spider neurotoxins. *Clin. Exp. Pharmacol. Physiol.* 2002; 29(9): 785-794]. These toxins show promise for development of recombinant biopesticides for control of insecticide-resistant agricultural pests [Nicholson and Graudins, ibid]. Sequential alanine substitutions along the peptide chain of the insect-specific toxins of the funnel-web spiders in which each amino acid residue is separately replaced with alanine demonstrated critical features necessary for insecticidal activity of the toxins [Tedford et al. 2004, ibid. and Tedford et al. Functional significance of the β-hairpin in the insecticidal neurotoxin omega-atracotoxin-Hv1a. *J. Biol. Chem.* 2001; 276(28): 26568-26576]. A more efficient method for producing large numbers of toxin variants that are potentially more effective against insects would be to substitute each amino acid in the toxin peptide with all 20 possible amino acids rather than just one.

The selective spider venom peptide, lycotoxin-1 (also known as lycotoxin-I), from wolf spider (*Lycosa carolinensis*) venom, is a small 25 amino acid peptide that demonstrates both antimicrobial and insect neuroactive properties [Yan and Adams. Lycotoxins, antimicrobial peptides from venom of the wolf spider *Lycosa carolinensis*. *J. Biol. Chem.* 1998; 273(4): $2059^{-2066}$. and Kourie and Shorthouse. Properties of cytotoxic peptide-formed ion channels. *Am. J. Physiol. Cell Physiol.* 2000; 278: C1063-C1087], which from its amphipathic nature and physiological actions appears to function as a pore former to increase membrane permeability, dissipate voltage gradients, and effect lysis of insect cells. Antimicrobial peptides for a related species of *Lycosa* indicate that some variation in peptide sequence is possible without losing biological activity [Budnik et al. De novo sequencing of antimicrobial peptides isolated from the venom glands of the wolf spider *Lycosa singoriensis*. *J. Mass Spectrom.* 2004; 39(2): 193-201].

SUMMARY OF THE INVENTION

We have now discovered novel lycotoxin-1 peptide variant sequences which exhibit increased insecticidal activity. Substitution of both a proline for the lysine at amino acid position 24 and a tryptophan for the leucine at amino acid position 25 of the wild-type amino acid sequence for lycotoxin-1, increases the insecticidal activity of the peptide. Moreover, further substitution of amino acids 8, 9 or 10 of the lycotoxin-1 wild-type amino acid sequence, specifically substituting a histidine for the phenylalanine at amino acid position 8, a glutamine for the glycine at amino acid position 10, or a serine for the leucine at amino acid position 9, provides an even greater increase in insecticidal activity. In addition to changes in the lycotoxin-1 amino acid sequence, the addition of an enterokinase K recognition site, DDDK, to the N-terminus of the lycotoxin-1 peptide increases insecticidal activity further still. The invention also includes isolated nucleic acid sequences encoding the lycotoxin-1 peptide variants, expression vectors containing these sequences, microorganisms or other host cells transformed with these vectors, and recombinant methods for producing the peptides.

In accordance with this discovery, it is an object of this invention to provide novel lycotoxin-1 peptides having improved insecticidal activity.

Another object of this invention is to provide novel lycotoxin-1 peptides possessing not only improved insecticidal activity, but also antimicrobial activity.

A further object of this invention is to provide the nucleic acid sequences which encode the mutant lycotoxin-1 peptides, which may be used to provide recombinant nucleic acid molecules containing the nucleic acid sequences for insertion into host cells and expression of the peptides therefrom.

Yet another object of this invention is to provide recombinant yeast cells which are effective for ethanol production and which also express novel lycotoxin-1 peptides having improved insecticidal activity as well antimicrobial activity.

A still further object of this invention is to provide a method for ethanol fermentation with no or reduced addition of exogenous antimicrobial agents for control of contaminants, and wherein the by-product yeast cells from the fermentation are valuable as insecticidal agents.

Other objects and advantages of this invention will become readily apparent from the ensuing description.

BRIEF DESCRIPTION OF THE DRAWINGS

FIG. 1 shows a Schematic drawing of INVSc1 yeast strain transformed with vector 1, pSUMOduo/URA/His XI, and with vector 2, pSUMOduo/TRP/HisLyt-1AASM, to give pSUMOduo/URA/His XI-pSUMOduo/TRP/HisLyt-1AASM-INVSc1 (INVSc1-XI-Lyt-1), in Example 1.

DEFINITIONS

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In procaryotes and some fungi, for example, the exogenous DNA may be maintained on an episomal element such as a plasmid. With respect to most eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

In the following description, the nomenclature used to define the peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

The instant invention provides mutants or variants of the lycotoxin-1 peptide which exhibit significantly increased insecticidal activity relative to the wild-type lycotoxin-1 produced by the Wolf spider (*Lycosa carolinensis*), as well as antimicrobial activity. These lycotoxin-1 peptide variants of the invention are produced by substitution of a proline and a tryptophan for the lysine and leucine at amino acid positions 24 and 25, respectively, of the wild-type amino acid sequence of lycotoxin-1 peptide. Thus, as the native or wild-type amino acid sequence of lycotoxin-1 is IWLTALKFLGKHAAKHLAKQQLSKL (Sequence ID No. 1), a first preferred variant possessing the above-mentioned substitutions is represented by the amino acid sequence IWLTALKFLGKHAAKHLAKQQLSPW (Sequence ID No. 2). The insecticidal activity of the lycotoxin variants of this invention may be further increased by also substituting one or more of the following: (a) a histidine for phenylalanine at amino acid position 8, (b) a glutamine for glycine at amino acid position 10, or (c) a serine for leucine at amino acid position 9 (where all amino acid positions are relative to the wild-type lycotoxin-1 sequence, Sequence ID No. 1, or the first variant of this invention, Sequence ID No. 2). Preferred embodiments of these lycotoxin variants possessing the above-mentioned substitutions at amino acids 24 and 25, as well as one of the substitutions at amino acids 8, 10 and 9, have the following amino acid sequences: IWLTALKHLGKHAAKHLAKQQLSPW (Sequence ID No. 3), IWLTALKFLQKHAAKHLAKQQLSPW (Sequence ID No. 4), IWLTALKFSGKHAAKHLAKQQLSPW (Sequence ID No. 5), respectively. In addition, the lycotoxin variant incorporating a glutamine for glycine at amino acid position 10 (Sequence ID No. 4) may optionally be further modified to substitute a histidine for glutamine at amino acid 20 and a serine for the glutamine at amino acid 21, providing the amino acid sequence IWLTALKFLQKHAAKHLAKHSLSPW (Sequence ID No. 6).

Insecticidal activity of the above-mentioned lycotoxin-1 peptide variants may be increased further still by the addition of an enterokinase K recognition site, DDDK, to the N-terminus of the peptide sequence. For the purposes of illustration and without being limited thereto, a variant comprising the enterokinase K recognition site and the proline and tryptophan substitutions at amino acids 24 and 25, respectively, is represented by the amino acid sequence DDDKIWLTALKFLGKHAAKHLAKQQLSPW (Sequence ID No. 7). Without wishing to be bound by theory, it is believed that this addition of the N-terminal enterokinase K recognition site facilitates the oral application of the lycotoxin-1 peptide variants as an insecticide by ensuring that the active toxin is not released until the enterokinase K tag is cleaved by trypsin in the insect gut. Once released in the gut, the active lycotoxin-1 peptide variants are then advantageously situated to penetrate insect cell membranes and subsequently lyse the cells, resulting in insect death.

The lycotoxin-1 peptide variants of this invention may be synthesized by any suitable method, such as exclusively solid-phase techniques, partial solid-phase techniques, fragment condensation, or classical solution addition. The amino acids of the compounds of the invention are typically joined to adjacent groups through amide linkages. For example, without being limited thereto, the peptide variants may be synthesized by methods well known to those skilled in the art of peptide synthesis, e.g., solution phase synthesis [see Finn and Hoffman, In "Proteins," Vol. 2, 3rd Ed., H. Neurath and R. L. Hill (eds.), Academic Press, New York, pp. 105-253 (1976)], or solid phase synthesis [see Barany and Merrifield, In "The Peptides," Vol. 2, E. Gross and J. Meienhofer (eds.), Academic Press, New York, pp. 3-284 (1979)], or stepwise solid phase synthesis as reported by Merrifield [J. Am. Chem. Soc. 85: 2149-2154 (1963)], the contents of each of which are incorporated herein by reference. However, the peptide variants are preferably produced by recombinant DNA techniques which are particularly suitable for large-scale use. Without being limited thereto, nucleotide sequences encoding the lycotoxin-1 peptide variants of this invention which are preferred for use in recombinant DNA techniques are described in detail in Example 1. In summary, the preferred nucleotide sequences encoding amino acid sequence ID Nos. 2, 3, 6, and 5, include:

CACCCATCATCATCATCATCATGATGATGATAAAATCTGGCTGACCGCGCTGAAATTTCTGGGC AAACATGCGGCGAAACATCTGGCGAAACAGCAGTTGTCGCCATGG (Sequence ID No. 8), CACCCATCATCATCATCATCATGATGATGATAAAATCTGGCTGACCGCGCTGAAACACCTGGGC AAACATGCGGCGAAACATCTGGCGAAACAGCAGTTGTCGCCATGG (Sequence ID No. 9), CACCCATCATCATCATCATCATGATGATGATAAAATCTGGCTGACCGCGCTGAAATTTCTGCAG AAACATGCGGCGAAACATCTGGCGAAACACAGTTTGTCGCCATGG (Sequence ID No. 10), and CACCCATCATCATCATCATCATGATGATGATAAAATCTGGCTGACCGCGCTGAAATTTAGTGGC AAACATGCGGCGAAACATCTGGCGAAACAGCAGTTGTCGCCATGG (Sequence ID No. 11), respectively.

Synthesis by the use of recombinant DNA techniques, for the purpose of this application, should be understood to include the suitable employment of structural genes coding for the sequence as specified hereinafter. The synthetic peptides may also be obtained by transforming a microorganism using an expression vector including a promoter or operator, or both, together with such structural genes and causing such transformed microorganisms to express the peptide.

The DNA sequences encoding lycotoxin-1 peptide variants can be used to prepare recombinant DNA molecules by cloning into any suitable vector. A variety of vector-host cell expression systems may be employed in practicing the present invention. Strains of yeast, *Saccharomyces cerevisiae*, such as described in the Example hereinbelow and in U.S. Provisional patent application Ser. No. 61/101,399 (filed Sep. 30, 2008, the contents of which are incorporated by reference herein) for fuel ethanol production, are particularly preferred. However, the novel invention described here can be applied with numerous hosts that would desirable. Host strains may be of bacterial, fungal, or yeast origin. Ascertaining the most appropriate host-vector system is within the skill of the person in the art.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al. [Molecular Cloning: A Laboratory Manual, Cold Springs Harbor Laboratory, 1989] or Ausubel et al. [Current Protocols in Molecular Biology, John Wiley & Sons, Inc, 1995], the contents of each of which are herein incorporated by reference. Further, the vectors may be non-fusion vectors (i.e., those producing the peptides of the invention not fused to any heterologous polypeptide), or alternatively, fusion vectors (i.e., those producing the peptides fused to a vector encoded polypeptide). The fusion proteins would of course vary with the particular vector chosen.

In accordance with a preferred embodiment, the vectors are the small ubiquitin-like modifier (SUMO) yeast expression vectors described by Butt et al. (2005) and Malakhov et al. (2004), the contents of each of which are incorporated by reference herein. This vector system effectively allows the expression of numerous genes simultaneously. This plasmid system is preferably used for transformation and expression of the lycotoxin-1 variant peptide encoding genes, as well as both XI and XKS in *S. cerevisiae* to facilitate ethanol fermentation.

Regardless of the specific vector utilized, various sites may be selected for insertion of the isolated DNA sequences. These sites are usually designated by the restriction enzyme or endonuclease that cuts them.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those skilled in the art. None of these factors alone absolutely controls the choice of insertion site for a particular polypeptide. Rather, the site chosen reflects a balance of these factors, and not all sites may be equally effective for a given protein.

The nucleotide sequences comprising the lycotoxin-1 variant peptide encoding genes may be inserted into the desired vector by known techniques. If, however, the vector is to serve as an expression vector, the vector should have a promoter, and the DNA sequences should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eucaryotic). Alternatively, any or all of the above control sequences may be ligated to the coding sequence prior to insertion into the vector.

DNA constructs may be introduced into the appropriate host by numerous methods described in the technical and scientific literature. Transformation of bacteria or yeast may be performed using standard techniques described in Maniatis et al., supra. Techniques for transforming filamentous fungi may include those described by Goosen et al. [Handbook for Applied Mycology, Arora, Elander & Mukerji, eds. (1992) pp. 151-195] and May et al. [Applied Molecular Genetics of Filamentous Fungi, Kinghorn and Turner, eds. (1992) pp. 1-27]. Transformations with yeast are described in Example 1 and application Ser. No. 61/101,399, filed Sep. 30, 2008.

In general, linear or circular DNA constructs may be introduced into the host by techniques utilizing protoplast fusion, polyethylene glycol, liposomes, lithium acetate, electroporation, physical damage, biolistic bombardment, or *Agrobacterium* mediated transformation.

Successful transformants may be isolated by using markers, contained on the expression vectors, which confer a selectable trait to the transformed yeast host. These may include nutritional selection related to substrate utilization (such as, growth on acetamide containing medium) or prototrophy of a required growth product (such as, arginine, leucine, or uracil). Dominant selectable markers (such as, resistance to ampicillin, G418, hygromycin, and phleomycin) are also useful in selecting transformants that have taken up the introduced DNA construct.

The DNA construct may be replicated autonomously or integrated into the genome of the host. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

As a practical matter it is anticipated that compositions of the lycotoxin-1 peptide variants may be prepared by formulating the compounds with an agriculturally acceptable inert carrier. Although a variety of solvents may be used, water is preferred. The peptides may also be formulated with solid inert carriers such as talc, clay or vermiculite, or incorporated into conventional controlled release microparticles or microcapsules. In addition, the compounds may be optionally formulated in combination with conventional insect attractants, baits, or other chemical or biological insecticides.

In accordance with a preferred embodiment described in the Example, yeast strains which are engineered for enhanced fuel ethanol production are also engineered to express the gene encoding a lycotoxin-1 peptide variant. Without being limited thereto, particularly preferred engineered yeast strains for use herein are described in application Ser. No. 61/101,399, filed Sep. 30, 2008, the contents of which are incorporated by reference herein. After use in the ethanol fermentation, the yeast may be recovered and pelletized for delivery of the insecticidal peptide within the yeast to the desired locations for insect control application. In this embodiment, the lycotoxin-1 peptide variants pass through the yeast cell membrane to the cell surface in vesicle and non-vesicle-mediated routes, possibly as a dimer, and thus are readily separated from the cells. Because the lycotoxin-1 peptide variants can expand the membrane surface of the yeast cell and allow dimer formation, release from the cell and activation of the peptide is delayed until the peptide is ingested by the insects. Consequently, the yeast expressing the lycotoxin-1 peptide variants acts as a capsule to conceal the toxin from the insect, increasing the insect's consumption of the peptides and ensuring that the insect will consume a lethal dose thereof.

The lycotoxin-1 peptide variants of this invention may be applied directly to the target insects (i.e., larvae, pupae and/or adults), or to the locus of the insects. However, because the peptide variants are effective when ingested by the insect, the peptides are preferably administered orally. Thus, they are preferably applied to the insect diet. The compounds are administered in an amount effective to induce the desired response as determined by routine testing. For example, where the desired effect is pest mortality, an "effective amount" is defined herein as those quantities which will result in a significant mortality rate in a test group as compared to an untreated control. The actual effective amount will of course vary with the specific lycotoxin-1 peptide variant, the target insect and its stage of development, and the application technique, and may be readily determined by the practitioner skilled in the art by routine testing. When determining effective amounts, it is understood that these lycotoxin-1 peptide variants need not be applied in amounts as great as the natural lycotoxin-1 peptide to kill the insects, particularly when employing the enterokinase K N-terminal tag. Without being limited thereto, it is envisioned that when administering the lycotoxin-1 peptide variants by ingestion, effective insect death may be achieved using concentrations between about 0.1 to 1.0% (measured by weight of the peptide in the bait).

It is envisioned that the compounds encompassed herein may be effective for controlling a variety of insects. Without being limited thereto, pests of particular interest are agronomically or commercially important insects, especially the fall armyworm (*Spodoptera frugiperda*).

In an alternative embodiment, the lycotoxin-1 peptide variants may be used as tags for expression of other heterologous proteins in transformed microorganisms, including yeast, or to carry or deliver a fused or attached peptide across the cell membrane of target cells of interest. For example, the peptide of Sequence ID No. 2 (also referred to as C3 herein) is capable of crossing cell membranes, and is transported extracellularly to the outside of the cell membrane, after being produced by a transformed host cell, where it can then be removed with a solvent such as ethanol. This property enables the C3 peptide to function as a carrier to transport an attached fusion protein from inside the cell where it is produced to the cell surface where it may be readily recovered. Suitable recombinant techniques for the production of such fusion proteins herein are well known in the art as described above. Alternatively, it is envisioned that the C3 peptide may be fused or otherwise chemically coupled to another compound to enhance the delivery of that compound across the cell membrane and into a target cell. This technique may be particularly suited to the delivery of pharmaceutical agents into the interior of targeted cells. In yet another embodiment, we have discovered that expression of the lycotoxin-1 peptide variant of Sequence ID No. 5 (also referred to as C6 herein) in a transformed host cell inherently causes a significant build-up of intracellular membranes (tubules) therein. As a result, expression of C6 also causes a significant build-up of proteins in the cell interior. Thus, cells co-transformed with the C6 and another heterologous protein of interest will express and accumulate significantly greater quantities of that protein than previously attainable. In this embodiment, the C6 peptide is preferably, but not limited to, expression as a fusion product with the heterologous protein of interest.

The following examples are intended only to further illustrate the invention and are not intended to limit the scope of the invention which is defined by the claims.

EXAMPLE 1

A multiplex method was used to develop lycotoxin-1 variant peptides having increased activity against a representative insect pest, the fall armyworm (*Spodoptera frugiperda*). Coupled with this methodology, we used the small ubiquitin-like modifier (SUMO) yeast expression vectors [Malakhov et al. SUMO fusions and SUMO-specific protease for efficient expression and purification of proteins. *J. Struct. Funct. Genomics* 2004; 5: 75-86. and Butt et al. SUMO fusion technology for difficult-to-express proteins. *Protein Expr. Purif.* 2005; 43: 1-9] to produce the large amounts of properly folded mutant peptides required for screening, and performed an initial screen of multiplexed cultures from which individual variants with enhanced lethality were then identified. These mutant peptides were produced by an ethanologenic yeast strain that grew on xylose plates. An enterokinase K (EntK) site was placed in front of the lycotoxin-1 ORF, which was then inserted into the SUMO vector so that after high levels of toxin are expressed in the yeast cells, the SUMO tag is quickly cleaved by the yeast protease (Ulp1), but active toxin is not released until the EntK tag is cleaved by trypsin in the insect gut killing the insect ('Trojan horse' strategy).

Materials and Methods

Production of pYES2-DEST52 NNR Mutant Lycotoxin-1 Library in INVSc1 Yeast Strain Two oligomers, each representing part of the sequence for lycotoxin-1 from *L. carolinensis* [Yan and Adams, ibid], were synthesized and annealed together. The annealed long oligomers were filled in with Taq polymerase using the ABI high fidelity kit as described previously [Hughes et al. Development of a liquid handler component for a plasmid-based functional proteomic robotic workcell. *J. Assoc. Lab. Autom.* 2005; 10(5): 287-300]. The PCR product representing the complete wild-type lycotoxin-1 (Lyt-1) sequence was purified, TOPO-cloned into pENTR D TOPO, and moved into pYES2-DEST52 yeast expression vector, a URA-selectable plasmid having a gal10 promoter (Invitrogen) for maximum expression in the INVSc1 yeast strain, using LR clonase according to the Invitrogen LR clonase II kit directions. The LR clonase reaction was transformed into TOP 10 competent cells and recovered on AMP 50 plates (Teknova), the resulting colonies were picked, and plasmids were prepared and transformed into INVSc1 yeast as described previously [Hughes et al. 2005, ibid]. The yeast was plated onto complete minimal (CM) galactose URA-selective agar to recover transformants. In addition, a library of mutagenized lycotoxin-1 ORFs was produced using an NNN mutagenesis strategy. Mutant clone #59 (also called C3) that was subsequently used for further mutagenesis via amino acid scanning mutagenesis (AASM) was obtained from this library of NNN mutants, in which the codons for amino acids of the wild-type Lyt-1 peptide were mutagenized. Targeted mutagenesis of all codons of wild-type Lyt-1 was accomplished by creating a PCR primer set of synthetic oligonucleotides consisting of a long forward primer with a sequence the same as that of the wild-type Lyt-1 ORF and a reverse primer (antisense strand) differing from the wild-type ORF. This primer contained any nucleotide in the first and second positions and a pyrimidine in the last position (NNN) for all codons of the ORF. Consequently the sense strand contained the complementary sequence. This strategy generates a library of ORFs that code for all possible amino acids at each of the codon positions of the Lyt-1 peptide. Methods for topoisomerase ligation of mutagenized PCR products into pENTR D TOPO, transformation into TOP 10 *Escherichia coli* cells, and subsequent plasmid preparation were performed. Thirty-two colonies with sequence-verified inserts from the pENTR D TOPO library were picked in triplicate into a 96-well plate and the mutagenized clones were inserted using LR clonase into pYES2-DEST52 for transformation into INVSc1 yeast and recovery on CM galactose URA-selective medium plates. The yeast strains with the expression plasmids carrying inserts for the peptide toxins were grown on CM galactose URA-selective plates and cultured in 50 ml defined CM galactose URA-selective liquid medium for scale up. Yeast cultures were grown, pelleted, lyophilized, mixed with insect diet, and placed on a disk on agar in a Petri dish for the initial armyworm larvae assay.

Construction of pSUMOduo Two-Vector System for Simultaneous Expression of Xylose Isomerase and Value-added Product Our objective was to express a value-added product, such as a bioinsecticide, in an ethanologenic yeast strain capable of utilizing xylose as well as glucose (FIG. 1). For the initial screen that identified clone #59, the mutant lycotoxins were placed into the yeast expression vector pYES2-DEST52 having a galactose-inducible promoter. It would not be possible to use this promoter to express the mutagenized lycotoxin-1 library in a commercial yeast strain that would also need to be evaluated for growth on pentose sugars in the absence of hexose sugars. It was determined that moving the lycotoxin-1 library into an expression vector with a constitutive ADH promoter would produce the highest levels of xylose utilization in a yeast strain engineered for overexpression of xylose isomerase (XI) [Kuyper et al. High-level functional expression of a fungal xylose isomerase: the key to efficient ethanolic fermentation of xylose by *Saccharomyces cerevisiae? FEMS Yeast Res.* 2003; 4(1): 69-78. Kuyper et al. Minimal metabolic engineering of *Saccharomyces cerevisiae* for efficient anaerobic xylose fermentation: a proof of principle. *FEMS Yeast Res.* 2004; 4(6): 655-664. and Kuyper et al. Metabolic engineering of a xylose-isomerase expressing *Saccharomyces cerevisiae* strain for rapid anaerobic xylose fermentation. *FEMS Yeast Res.* 2005; 5(4-5): 399-409]. The pSUMOduo high-copy expression vector set, containing the protease-cleavable yeast SUMO tag (Smt3) behind an ADH promoter and also a T7 in vitro modified promoter, was selected [Malakhov et al., ibid].

For the novel yeast episomal pSUMOduo high-level expression vector set [Malakhov et al. ibid. and Butt et al. ibid], the protease-cleavable yeast SUMO tag (Smt3) was placed in front of an Invitrogen Gateway cassette, producing an AMP-selectable destination vector for recombination of library inserts. The SUMO insert ORFs were expressed behind an ADH promoter and also a T7 in vitro modified promoter. Two vectors were produced, pSUMOduo/URA and pSUMOduo/TRP, each one having a different yeast selectable marker (for uracil or tryptophan prototrophy, respectively) and each used for expression of a different ORF of interest: Piromyces XI or lycotoxin-1 peptide. The vectors contain the yeast high-copy 2μ origin of replication, to give a copy number of roughly 20 per yeast cell [Christianson et al. Multifunctional yeast high-copy-number shuttle vectors. *Gene* 1992; 110(1): 119-122].

The first plasmid, pSUMOduo/URA, was constructed as follows. First, a Gateway cassette fragment (Gateway Vector Conversion System, Invitrogen) containing attR1-ccdBCm$^R$-attR2 was amplified by PCR with primers containing BbsI restriction sites designed to generate ACCT and GATC overhangs, then subcloned into BsaI/BamHI-digested pSUMO (aka pET24-6×His-SUMO) [Malakhov et al. ibid] to construct the plasmid pSUMO-Gateway. A $P_{T7}$-His$_6$-Smt3-Gateway cassette$T_{T7}$ fragment was then PCR-amplified from pSUMO-Gateway, digested with EcoRV and BbsI to generate a blunt end and a GATC overhang, and subcloned into a SmaI/BglII fragment of pRS306-$P_{ADH}$ [Sterner et al. Functional organization of the yeast SAGA complex: distinct components involved in structural integrity, nucleosome acetylation, and TATA-binding protein interaction. *Mol. Cell. Biol.* 1999; 19(1): 86-98] containing the *E. coli* amp$^R$ marker, the yeast URA3 marker, and the promoter of the yeast ADH1 gene. The resulting plasmid was digested with SapI and ligated with a SapI fragment from pRS426 [Christianson et al. ibid] containing the yeast 2μ origin of replication. QuikChange mutagenesis [Wang and Malcolm. Two-stage PCR protocol allowing introduction of multiple mutations, deletions and insertions using QuikChange Site-Directed Mutagenesis. *Biotechniques* 1999; 26(4): 680-682] was then used on the resulting plasmid to delete two extraneous, tandem PT7 sequences present in the vector backbone from the previous construction of pRS306-P$_{ADH}$ [Sterner et al. ibid].

To replace the URA3-selectable marker in pSUMOduo/URA with TRP1 and create the other vector of the 2-vector system, the TRP1 sequence was amplified from pGBKT7 vector (Clontech) with oligos (CGCGAGCTAGC-CGCGCGTTTCGGTGATGACGGTGA) and (CGC-GACGCGTGATCGGCAAGTGCACAAACAATACT) (Sequence ID Nos. 12 and 13, respectively). Inserts were then digested with NheI and MluI and cloned into similarly digested pSUMOduo/URA vector.

The Piromyces XI wild-type ORF [Kuyper et al. 2003. ibid] with His tag was placed into pENTR D TOPO, cloned into vector 1, pSUMOduo/URA, of this 2-vector system (LifeSensors, Malvern, Pa.), and transformed as described previously [Hughes et al. 2005. ibid] into INVSc1 yeast (Invitrogen), a fast growing diploid strain ideal for expression, which does not sporulate well and carries the mutations MATalpha-his3D1-leu2-trp1-289-ura352 MAT-his3D1-leu2-trp1-289-ura3-52, to produce the strain pSUMOduo/URA/His XI-INVSc1 (INVSc1-XI).

Production of pSUMOduo/TRP/Lyt-1 AASM Mutant Library in INVSc1-XI Yeast Strain

The pENTR D TOPO library of ORFs for mutant lycotoxin-1 sequences produced by AASM from clone #59 was placed into vector 2, pSUMOduo/TRP, of the 2-vector system (LifeSensors, Malvern, Pa.). The library was designed to code for all possible 20 amino acids at each of the 25 amino acid positions in lycotoxin-1 from wolf spider *L. carolinensis* [Yan and Adams. ibid]. This set of multiplexed ORF inserts in pENTR D TOPO was moved by LR clonase into the pSUMOduo/TRP vector to produce the pSUMOduo/TRP/His-Lyt-1 AASM library. This was mass-transformed into the INVSc1-XI strain to produce pSUMOduo/URA/His XI-pSUMOduo/TRP/HisLyt-1, AASM-INVSc1 (INVSc1-XI-Lyt-1) strains in each of 25 multiplexed wells, one well per amino acid position mutation, with all 20 amino acid possibilities for that position in each well.

Screening of Lycotoxin-1 Mutants for Lethality

Initially, for testing the NNR mutants, the yeast cultures were pelleted, lyophilized, mixed in water used to rehydrate lyophilized pinto-bean-based insect diet [Dowd et al. Oral toxicity of beta-N-acetyl hexosaminidase to insects. *J. Agric. Food Chem.* 2007; 55(9): 3421-3428], and placed on a Teflon disk at the center of a 32 mm Petri dish containing 3% agar. Armyworm larvae were added to the dish where they could move along the moist agar surface to the yeast culture area. The armyworms were obtained from a laboratory colony in Illinois associated with the USDA, Crop Bioprotection Research Unit, and were propagated from eggs in an insectarium at NCAUR. Twenty newly hatched larvae were used per treatment. Yeast carrying a GUS plasmid was used as a control. The number of dead armyworms was counted each day of the assay.

Because it was found that assays using growing yeast appeared to give more sensitive bioassay results, the testing of the AASM mutants was performed by applying the armyworm larvae directly to plates containing areas of growing yeast. Samples of the transformation reactions from each of the multiplex wells were recovered on 86×128 mm rectangular CM glucose URA/TRP-selective plates for 2 days at 30° C. and diluted 10.000-fold in sterile water; then 200 μl was spotted onto the respective CM xylose URA/TRP-selective plates and allowed to grow for 3 days to generate a yeast growth area (spot) expressing toxins. The size of the spot was recorded and used to normalize the percent killed, since the percent is a function of the amount of yeast encountered. Twenty newly hatched armyworm larvae were added to the growth spot on the plate, the plate was covered with a lid having five small 0.4 mm openings in the center protected with cotton organdy cloth, and the lid was sealed to the plate with Microseal 'A' film (MJ Research, Waltham, Mass.) cut so that a gasket 5-mm wide could seal the edges. The plates were scored for the number of dead armyworms daily after adding the larvae until the assay was ended. Results from days 1 and 2 were of the greatest importance for a commercially viable insecticide. The multiplexed wells having the mutants showing greatest lethality (positions 8, 9, and 10) were selected and the multiplexed wells containing the lycotoxin-1 inserts in pENTR D TOPO corresponding to those positions were transformed into TOP 10 cells, single colonies picked from spread plates, and a plasmid preparation performed. The sequences of 90 AASM variant single isolates picked from the three most lethal multiplexed wells were determined. Forty-five of these had inserts with complete sequences in the correct orientation. Nine were C3, while 36 of them were unique variants and these were selected for the second lethality assay. They were moved into pSUMOduo/TRP via LR clonase, retransformed into INVSc1-XI yeast, and recovered on CM glucose URA/TRP-selective plates. Single colonies with sequence-verified inserts were picked into CM glucose URA/TRP-selective liquid medium, grown, and diluted 10,000-fold. A 100 μl sample was spotted onto CM xylose URA/TRP-selective plates and analyzed for lethality, along with samples containing C3, in quadruplicate, with 20 newly hatched armyworm larvae added to each plate. The variants were scored for dead armyworms and the percent killed was calculated.

Polyacrylamide Gel Electrophoresis and Western Blot Procedure

Transformed yeast strains carrying the pSUMOduo plasmids, each with a different selectable marker, were inoculated into 1.0 ml of the respective selective medium and grown for 2 days at 30° C. in deepwell plates. The resulting cultures were spun down at 4000 rpm for 20 min in a swinging bucket centrifuge with plate carriers, the supernatant was discarded, and the pellet in the first well of the first column of the plate was resuspended by vortexing with 250 μl Y-PER lysis buffer. This solution was used to resuspend the pellets in each successive well of the first column. The solution was transferred to the first well of the next column and vortexed to resuspend the pellet. The process was repeated until all the pellets were combined and resuspended in the last well of the last column. This 250-μl sample was pipetted into a 1.5-ml tube and incubated at 4° C. with rotating for 3-4 h. A 30-μl aliquot from this tube was pipetted into the wells in an MJ plate and 30 μl of 2× tris-glycine SDS loading buffer (Invitrogen) with β-mercaptoethanol (BME) was added to each well. To the remaining 220 μl of sample in the 1.5-ml tube was added 100 μl of Super Flow Ni beads (Qiagen), and the sample was incubated at 4° C. with rotating for approximately 3 h. The sample was centrifuged at 13000 rpm for 2 min and 30 μl of the supernatant was pipetted into a new 1.5-ml tube. Thirty microliters of 2× tris-glycine SDS loading buffer with BME was added. These samples and the samples in the MJ plates were heated to 95° C. for 10 min, loaded onto 1.5-mm thick 16% trisglycine 15-well SDS-PAGE gels (Invitrogen), and run at 110 V for 150 min. The gel was assembled into an X-Cell Novex box and run in 1× tris glycine running buffer. It was removed and transferred to polyvinylidene difluoride (PVDF) cut sheets (Invitrogen). The transfer took place in the Novex transfer apparatus with 1× transfer buffer (Invitrogen) for 10 h at a constant current of 200 mA. Westerns were chromogenic and performed with the Western Breeze kit (Invitrogen) according to the manufacturer's directions using 30 µl of a Qiagen mouse anti-penta-His antibody resuspended in 1 ml of sterile 1× phosphate buffered saline (PBS) with magnesium and calcium (secondary antibody was anti-mouse antibody conjugated to alkaline phosphatase). Western blot images were captured using the Alpha Innotech 3400.

Scanning Electron Microscopy

Yeast cells from the plate were suspended in saline (0.85% NaCl) and centrifuged to remove the residual medium. Following a modified procedure of Bang and Pazirandeh [Bang and Pazirandeh. Physical properties and heavy metal uptake of encapsulated *Escherichia coli* expressing a metal binding gene (NCP). *J. Microencapsul.* 1999; 16(4): 489-499], the cell pellet was suspended and fixed in 2.5% glutaraldehyde prepared in 100 mM cacodylate buffer, pH 7.2, for 1 h on ice. To remove remaining glutaraldehyde, the cells were rinsed with the buffer twice and then with distilled water once, allowing several minutes for each step. The cells were dehydrated in solutions containing 50, 70, 80 and 100% ethanol successively for 15 min for each treatment. Cells were mounted on the aluminum stub and placed in the desiccator to dry overnight or until needed. The samples were subjected to scanning electron microscopy and analysis (Zeiss Supra 40 VP).

Results and Discussion

Lethality to Armyworms of NNR Mutant Lycotoxin-1 Library in INVSc1 Yeast Strain (Initial Screen)

The lyophilized yeast cultures expressing wild-type lycotoxin-1 and the library of mutagenized lycotoxin1 ORFs that was produced using the NNN mutagenesis strategy were each mixed with rehydrated lyophilized insect diet and the mixture was placed on the Teflon feeding disk at the center of a Petri dish [Dowd et al. ibid]. When the armyworm larvae were added, they tracked the material off the disk onto the agar in the dish. The yeast became rehydrated and began to grow and express toxin. The armyworms not only ingested the yeast but also carried it across the agar producing numerous yeast colonies. One of the yeast cultures was highly lethal to the armyworms. This yeast strain was expressing a lycotoxin-1 variant, identified as clone #59 (designated C3 in this paper), with the sequence $H_2NHHHHHH(6×His)DDDK(EntK)$ IWLTALKFLGKHAAKHLAKQQLSPWCOOH Sequence ID No. 14), produced by the mutagenesis strategy in which the codons for the amino acids in the peptide were randomized for NNR. This C3 variant differed from wild-type lycotoxin-1 in the two amino acids at the carboxy terminus, with proline and tryptophan residues replacing the lysine and leucine residues at positions 24 and 25, respectively, in the wild-type lycotoxin-1. These initial screening results demonstrated that the solid agar plate would support the growth of the yeast colonies and indicated that the fall armyworm larvae would consume growing yeast cultures expressing pep-tide toxins. The lycotoxin-1 variant (C3) that was highly lethal to the armyworms in this initial evaluation was selected for further optimization by AASM. The wild-type lycotoxin-1 peptide was not found to be lethal in this initial screening. It is possible that wild-type Lyt-1 did not demonstrate lethality in this setting because the wild-type Lyt-1 form does not have the proper pharmacodynamic properties to reach the target site when administered orally. Prior work demonstrating activity of this peptide used injections or cell assays [Yan and Adams, ibid].

Strategy Using pSUMOduo Vector System

For the initial screen that identified C3, the NNR mutant lycotoxins were placed into the yeast expression vector pYES2-DEST52 having a galactose-inducible promoter. This promoter could not be used to express the mutagenized lycotoxin-1 library in a commercial yeast strain that would also need to be evaluated for growth on pentose sugars in the absence of hexose sugars. The pSUMOduo high-copy expression vector set, containing the protease-cleavable yeast SUMO tag (Smt3) behind an ADH promoter and also a T7 in vitro modified promoter [Malakhov et al. ibid], was selected to produce high levels of expression in the INVSc1 yeast strain engineered for xylose utilization (FIG. 1).

In nature, the SUMO modulates protein structure and function by covalently binding to the lysine side chains of the target proteins [Malakhov et al. ibid]. In genetic and functional proteomic studies, the SUMO gene fusion system can be used to improve expression and chaperone correctly folded proteins and peptides [Butt et al. ibid]. Yeast cells contain a protease (Ulp1 or SUMO protease 1) that can efficiently cleave a variety of SUMO fusions robustly and with great specificity [Malakhov et al. ibid]. The enzyme is active over a broad range of pH and temperature conditions. Attachment of SUMO to the N-terminus of proteins has been found to greatly enhance their expression. Vector 1 of the SUMO system was used to express the PCR-assembled XI ORF. The SUMO protease 1 (Ulp1) in yeast is highly efficient and cleaves the SUMO tag to completion giving large amounts of functional XI. Vector 2 was used for expression of the lycotoxin-1 clone library produced by AASM to allow automated high-throughput plasmid production and expression of this insecticidal peptide. This vector can be used for other optimized ORFs, such as cellulases, to produce improved yeast strains for industrial use in conjunction with the XI gene to enable xylose utilization. A third SUMO vector (LEU selectable) is available that would make possible introduction of additional clones of interest. These could be obtained from traditionally produced cDNA libraries using superscript reverse transcriptase or the FLEXGene collections [Zuo et al. PlasmID: a centralized repository for plasmid clone information and distribution. *Nucleic Acids Res.* 2007; 35: (Database issue): D680-D684] of expression-ready fully annotated inserts for whole library introductions or ordered grid transformations of select FLEXGene sets. This vector could allow expression of enzymes to improve tolerance, permit anaerobic growth on xylose, and increase ethanol output in industrial yeast strains.

Lethality to Armyworms of AASM Mutant Lycotoxin-1 Library in INVSc1-XI Yeast Strain Lethality testing on fall armyworm larvae of the multiplexed cultures of INVSc1-XI-Lyt-1 yeast strains grown on CM xylose URA/TRP-selective plates indicated that variants with mutations at positions 8, 9, or 10 gave the greatest effect at days 1 and 2, while those having mutations at positions 5, 6, 7, or 11 showed the next most lethal effect. Mutations at positions 14, 15, 19, 20, 21, or 23 were less effective and mutations at positions 4, 12, 13, 16, 17, 18, or 22 showed no effect on the fall armyworms (Table 1). All variants contained the mutations in the parent clone #59 (designated C3 herein), which had proline and tryptophan at positions 24 and 25, respectively, adjacent to the carboxy terminus. Wild-type lycotoxin-1 has a lysine residue at 24 and a leucine at 25.

Single colonies were picked from the multiplexed wells for the mutation positions showing greatest lethality. Growing yeast spots containing the individual variants were tested for lethality to fall armyworm larvae. The results for the parent variant (C3) and for the three most lethal mutations derived from C3 are presented in Table 2. Percent dead on day 2 for C3, B9, A6, and C6 were 71, 97, 74, and 100%, respectively (Table 2). The two AASM mutants B9 and C6 were more lethal than the NNR mutant C3. The numbers are normalized for diameter of the colony on the xylose plates. A test for normality, performed using SAS Proc Univariate (SAS Institute 1999), indicated that the mortality data did not follow a normal distribution, and therefore analysis of variance was not appropriate. Frequency analysis was performed using SAS Proc Freq (SAS Institute 1999) with data adjusted for colony size and assuming a conservative 20-insect sample for each treatment. Under these conditions, relative mortality caused by mutants B9 and C6 was significantly greater than mortality caused by mutants C3 and A6 ($P<0.05$). Mortality caused by mutant C6 compared to B9 and mortality caused by A6 compared to C3 were not significantly different in this analysis.

The function of lytic peptides such as lycotoxin1 is to cause cell lysis by disrupting the cell membrane. Common features of these peptides include an overall basic charge, a small size (23-39 amino acid residues), and the ability to form amphipathic α-helices. They appear to disrupt the membrane lipid bilayer either by association with the amphipathic α-helix portion or by ion channel formation. In either case, an ordered secondary conformation such as an amphipathic α-helix and positive charge appear to participate in the lytic function [Julian and Jaynes. Methylated lysine-rich lytic peptides and method of making same by reductive alkylation. U.S. Pat. No. 5,717,064. Issued Feb. 10, 1998. Corzo et al. Oxyopinins, large amphipathic peptides isolated from the venom of the wolf spider *Oxyopes kitabensis* with cytolytic properties and positive insecticidal cooperativity with spider neurotoxins. *J. Biol. Chem.* 2002; 277(26): 23627-23637. and Duguid et al. A physicochemical approach for predicting the effectiveness of peptide-based gene delivery systems for use in plasmid-based gene therapy. *Biophys. J.* 1998; 74(6): 2802-2814]. The net positive charge promotes interaction with negatively charged prokaryotic membranes (normal mammalian cell membranes have more positive-charge character).

The sequence of the mutant peptides was designed to allow expression of high levels of appropriately folded, soluble peptides after ingestion by the insect before release of active toxin by trypsin in the insect gut. Out of all possible theoretical mutations created, the critical positions were found to be positions 8, 9, and 10. It is possible that the strains with the optimized clones had already been selected to some extent by lack of viability on xylose or toxicity to yeast. The screening process identified the yeast strains that tolerated the presence of the toxin and also grew aerobically on xylose. The fall armyworms willingly consumed the yeast cultures that were expressing the optimized variants and died.

The armyworms on the control plate, containing INVScI-XI yeast culture, are alive, have grown quite large, and are very active as seen by the trail of yeast colonies. The fact that the INVSc1-XI strain does not kill the armyworm larvae excludes the possibility that the alcohol has insecticidal activity since this strain would produce a quantity of ethanol similar to that produced by the INVSc1-XI-Lyt-1. Beyond 2 days some cannibalism occurred and it was difficult to observe unharmed worms as they first ate the yeast and then each other. On the other hand, the armyworms on the plates containing cultures expressing variants designated C3 (clone #59), A6, B9, and C6 are much smaller and mostly or all dead. An enlargement of one larva from each plate provides increased detail of the dead armyworms against the plate background. These cultures may be lethal because the expressed toxin is not immediately cleaved at the EntK site, giving so called Trojan horse peptides. The Lyt-1 peptide with the uncleaved EntK site is seen in the Western blot analysis.

The SUMO fusion technology used here in the second round of lycotoxin-1 peptide mutagenesis provides high levels of expression of the mutant toxins in the yeast strains and generates toxins that are lethal to the pests. When the sequence for the HisEntKLyt-1 is used with the SUMO vector, it is possible to express large amounts of engineered peptide for cleavage by endogenous yeast SUMO protease 1, which removes the SUMO tag after proper folding and increased solubility are accomplished [Malakhov et al. ibid]. The high levels of peptide with the uncleaved EntK site produced in the yeast cells are taken in by the armyworms, followed by release of active toxin by cleavage at the EntK site, DDDK, which is less active for insect gut trypsin than trypsin sites, permitting large amounts of toxin to get inside the armyworm before it is affected and stops ingesting the yeast. By consuming yeast expressing high levels of the peptide, the armyworms rapidly accumulate a lethal amount of toxin in their system before they are aware they have ingested it. Expression of the lycotoxin-1 variants did not affect the doubling time of the yeast cultures on glucose (1.9 h; SD 0.3; n=5; data not shown), indicating the toxin was not lethal to the yeast.

Western Blot Analysis of Variant Yeast Strains

Lysates prepared after growth on CM glucose URA/TRP-selective plates and run directly on a 16% polyacrylamide gel show three major bands for all four strains: 53.7 kD for the attB1His XI recombinant protein; 16.6 kD for the HisSUMO tag removed from both HisLyt-1 and His XI; and 10.7 kD for the attB1HisEntKLyt-1 fusion toxin. The band for the HisSUMO leader is twice as intense as either of the other two bands since it is released from both the XI protein and the lycotoxin-1 variants in those samples.

Lysates prepared after growth on CM glucose URA/TRP-selective plates and additionally subjected to Ni bead purification of the His-tagged proteins and then run on a 16% polyacrylamide gel show the same three bands (with a decrease in intensity of the 10.7 kD attB1HisEntKLyt-1 band) and an additional band at 21.4 kD, attributed to a dimer of the attB1HisEntKLyt-1 protein for all four strains. Dimer formation is postulated because in the Ni bead purification the beads concentrate the peptide on their surface and highly favor aggregation. Numerous amphipathic peptides are commonly thought to form multimeric pores in cell membranes [Kourie and Shorthouse, ibid]. In a model for pore formation in a membrane by magainin II, the molecules are arranged in dimers of α-helices aligned to form antiparallel amphipathic units. The amphipathic peptide, amyloid β-protein, associated with senile plaques in Alzheimer's disease, forms stable dimers [Garzon-Rodriguez et al. Soluble amyloid Aβ (1-40) exists as a stable dimer at low concentrations. *J. Biol. Chem.* 1997; 272(34): 21037-21044] as shown by fluorescence resonance energy transfer and gel filtration chromatography. Aggregate formation by amyloid β-protein has been studied using SDS-PAGE [Burdick et al. Assembly and aggregation properties of synthetic Alzheimer's A4/beta amyloid peptide analogs. *J. Biol. Chem.* 1992; 267(1): 546-554. and Soreghan et al. The influence of the carboxyl terminus of the Alzheimer Abeta peptide on its conformation, aggregation, and neurotoxic properties. *Neuromolecular Med.* 2002; 1(1): 81-94]. The attB1HisEntKLyt-1 monomer band on the Western blot gel is dramatically decreased in intensity as would be expected if it were being used to form dimer. The gel also shows that a large amount of toxin is still tagged with attB1HisEntK and so was being ingested by worms in the uncleaned form, supporting the 'Trojan horse' strategy.

Morphology of Yeast Strains

In scanning electron micrographs, INVSc1 yeast cells have the typical rounded appearance of the *S. cerevisiae* fast-growing diploid-type strain with limited sporulation and some bud scars visible. Cells of the INVSc1-XI yeast strain are larger and have a somewhat squared shape and uneven surface with dents, some quite deep, in the center, as well as slight linear indentations along the surface of the cell. These effects could be the result of interactions of the SUMO vector with the membrane. The structure of Smt3 consists of two α-helices and one β-sheet. The α1 helix is strongly amphipathic, with hydrophobic residues pointing inward and hydrophilic residues pointing into the solvent [Sheng and Liao. Solution structure of yeast ubiquitin-like protein Smt3: the role of structurally less defined sequences in protein-protein recognitions. *Protein Sci.* 2002; 11: 1482-1491]. Interactions of amphipathic peptides with cell membranes have been shown to produce significant perturbations in the cell structure [Lamazi ere et al. Non-metabolic membrane tubulation and permeability induced by bioactive peptides. *PLoS ONE* 2007; 2(2): e201]. These perturbations include membrane adhesions, vesicle aggregation, membrane tubulation, and invaginations. The change in the cells of the INVSc1-XI-Lyt-1 variants is even more striking. Cells of the INVSc1-XI-Lyt-1 yeast strain, expressing variants C3, A6, B9, and C6, have numerous bulges and irregularities on the surface suggesting that large amounts of material are present inside the cells. Cells of these four INVSc1-XILyt-1 strains also show dents similar to the INVSc1-XI strain. No dents, bulges, or irregularities are evident in the pictures of the INVSc1 strain. Localization of the peptide is strongly dependent on the charge and hydrophobic nature of the peptide and the charge on the cell membranes [Lamazi ere et al. ibid. Parenteau et al. Free uptake of cell-penetrating peptides by fission yeast. *FEBS Lett.* 2005; 579(21): 4873-4878 and Holm et al. Uptake of cell-penetrating peptides in yeasts. *FEBS Lett.* 2005; 579(21): 5217-5222]. Cells containing variant C3 have large amounts of matted material on the outside of the cells. Since all cells were prepared in the same way, it is unlikely to be an artifact of the preparation, but it is not clear if it affects lethality.

Mutations in Lycotoxin-1 Variants Showing Greatest Lethality

Sequence analysis of the most lethal toxin positions indicated mutations at position 8 in A6 from phenylalanine to histidine, at position 10 in B9 from glycine to glutamine, and at position 9 in C6 from leucine to serine. Additionally, in clone B9 there are PCR mutations in position 20 and 21, putting histidine and serine, respectively, in place of two glutamine residues. All three of these lethal clones also have mutations in positions 24 and 25 from lysine and leucine to proline and tryptophan, respectively, that were present in clone #59 (C3). A helical-wheel projection of the amphipathic peptide illustrates the lycotoxin-1 mutations relative to the hydrophobic and hydrophilic sections of the three-dimensional structure. All variants have mutations Lys24Pro and Leu25Trp. Additional mutations in A6 include (Phe8His), B9 (Gly10Gln, Gln20His, Gln21Ser), and C6 (Leu9Ser). The greatest lethality, 83-100% is found for variants having mutations in positions 8, 9, or 10.

The mutations in the lycotoxin-1 variants showing greatest lethality affect the amphipathic properties of the peptide structure by altering charge, steric effects, and polarity changes. The substitutions of proline and tryptophan replacing lysine and leucine at positions 24 and 25, respectively, have possible steric and charge effects. The change at position 24 increases the hydrophobic nature of the hydrophobic side of the helix and ensures two hydrophobic residues at the C-terminal, which have been found to be important for activity [Mayo et al. Structure-function relationships in novel peptide dodecamers with broad-spectrum bactericidal and endotoxin-neutralizing activities. *Biochem. J.* 2000; 9: 717-728], although the exact functional significance is unknown. Tryptophan residues in conjunction with lysines have also been shown to contribute to favorable interaction with negatively charged cell membranes. The substitution of a polar Ser residue for a neutral Leu residue at position 9 may increase the interaction with the interior of the cell membrane. The positively charged lysine core, with Lys residues at positions 7, 11, 15, and 19, is unchanged in the individual variants that showed the greatest lethality, and this region is increased in positive charge in optimized mutant A6, which has a phenylalanine to histidine mutation at position 8. This positively charged region is crucial for binding to negatively charged insect cell membranes [Mayo et al. ibid].

CONCLUSIONS

These bioinsecticidal peptides have potential as commercially valuable coproducts that can be expressed in yeast strains capable of converting cellulosic biomass into fuel ethanol in order to improve the cost effectiveness of the process. Toxins from spider venoms are promising from the perspective of pest resistance since they define new insecticide targets owing to specific actions to block insect voltage-gated $Ca^{2+}$ channels. The optimized toxin peptides are expressed and accumulate in large amounts in the ethanologenic yeast strains. The test insects are killed upon ingesting the yeast.

It is understood that the foregoing detailed description is given merely by way of illustration and that modifications and variations may be made therein without departing from the spirit and scope of the invention.

TABLE 1

Lethality to fall armyworms of multiplexed cultures of INVSc1-XI-Lyt-1 yeast strains with libraries of Lyt-1 variants grown for 3 days on CM xylose URA/TRP selective plates. Each multiplexed culture contained lycotoxin-1 variants with all possible amino acids at one of the 25 positions in the amino acid sequence. Twenty fall armyworm larvae were fed the culture and the number of dead worms was scored on day 1 and day 2. The percent killed was adjusted for the diameter of the yeast colony on the medium.

| Strain Carrying toxin with Mutation at aa Position | Armyworms killed day 1 (%) | Armyworm killed day 2 (%) |
|---|---|---|
| aa position 4 | 0.0 | 0.0 |
| aa position 5 | 0.0 | 47.3 |
| aa position 6 | 18.3 | 55.7 |
| aa position 7 | 19.5 | 83.3 |
| aa position 8 | 43.0 | 83.3 |
| aa position 9 | 44.3 | 92.7 |
| aa position 10 | 0.0 | 100.0 |
| aa position 11 | 0.0 | 47.0 |
| aa position 12 | 5.5 | 0.0 |
| aa position 13 | 4.9 | 5.6 |
| aa position 14 | 19.7 | 27.7 |
| aa position 15 | 16.5 | 17.8 |
| aa position 16 | 0.0 | 0.0 |
| aa position 17 | 0.0 | 0.0 |
| aa position 18 | 0.0 | 0.0 |
| aa position 19 | 0.0 | 27.8 |
| aa position 20 | 0.0 | 15.4 |
| aa position 21 | 0.0 | 37.9 |
| aa position 22 | 0.0 | 0.0 |
| aa position 23 | 0.0 | 27.8 |

TABLE 2

Lethality to fall armyworms of single colonies from the three most lethal multiplexed position mutations with sequence-verified lycotoxin-1 inserts grown on CMxylose URA/TRP selective plates for 3 days compared with the parent variant [clone #59 (C3)].
Fall armyworm mortality from single INVSc1-XI-Lyt-1 yeast strain isolates expressing Lyt-1 toxin variants grown on xylose plates

| Yeast strain | Day 1 (% killed) | Day 2 (% killed) |
|---|---|---|
| XI-yeast control | 0.0 | 0.0 |
| XI Lyt-1 C3 (template ORF #59, has mutations K24P and L25W) | 3.4 | 71.0 |
| XI Lyt-1 A6 (variant has mutations F8H, K24P, L25W) | 13.2 | 74.1 |
| XI Lyt-1 B9[a] (variant has mutations G10Q, Q20H, Q21S, K24P, L25W) | 0.0 | 97.2 |
| XI Lyt-1 C6[a] (variant has mutations L9S, K24P, L25W) | 3.7 | 100.0 |

Percent fall armyworms killed adjusted for colony use (4 plates averaged, each with 20 larvae added/plate)
[a]Mortality significantly greater than C3 and A6 ($P < 0.05$). C6 not significantly greater than B9. A6 not significantly greater than C3.

We claim:

1. A lycotoxin-1 peptide variant, wherein said lycotoxin-1 peptide comprises SEQ ID NO: 1, and said variant comprises a proline at amino acid position 24 and a tryptophan at amino acid position 25.

2. The lycotoxin-1 peptide variant of claim 1 further comprising a histidine at amino acid position 8.

3. The lycotoxin-1 peptide variant of claim 1 further comprising a glutamine at amino acid position 10.

4. The lycotoxin-1 peptide variant of claim 1 further comprising a serine at amino acid position 9.

5. The lycotoxin-1 peptide variant of claim 1 selected from the group consisting of C3 (Sequence ID NO: 2), A6 (Sequence ID NO: 3), B9 (Sequence ID NO: 6), and C6 (Sequence ID NO: 5).

6. The lycotoxin-1 peptide variant of claim 1 further comprising an enterokinase K recognition site, DDDK, at the N-terminus of said lycotoxin-1 peptide.

7. An isolated nucleic acid molecule comprising a nucleic acid sequence encoding a lycotoxin-1 peptide variant, wherein said lycotoxin-1 peptide comprises SEQ ID NO: 1, and said variant comprises a proline at amino acid position 24 and a tryptophan at amino acid position 25.

8. The isolated nucleic acid molecule of claim 7 comprising said nucleic acid sequence encoding said lycotoxin-1 peptide variant, wherein said lycotoxin-1 peptide variant further comprises a histidine at amino acid position 8.

9. The isolated nucleic acid molecule of claim 7 comprising said nucleic acid sequence encoding said lycotoxin-1 peptide variant, wherein said lycotoxin-1 peptide variant further comprises a glutamine at amino acid position 10, a histidine at amino acid position 20, and a serine at amino acid position 21.

10. The isolated nucleic acid molecule of claim 7 comprising said nucleic acid sequence encoding said lycotoxin-1 peptide variant, wherein said lycotoxin-1 peptide variant further comprises a serine at amino acid position 9.

11. The isolated nucleic acid molecule of claim 7 comprising said nucleic acid sequence encoding said lycotoxin-1 peptide variant, wherein said lycotoxin-1 peptide variant is selected from the group consisting of C3 (Sequence ID NO: 2), A6 (Sequence ID NO: 3), B9 (Sequence ID NO: 6), and C6 (Sequence ID NO: 5).

12. The isolated nucleic acid molecule of claim 11, wherein said nucleic acid sequence is selected from the group consisting of Sequence ID NO: 8, Sequence ID NO: 9, Sequence ID NO: 10, and Sequence ID NO: 11.

13. An isolated nucleic acid molecule comprising a nucleic acid sequence encoding a lycotoxin-1 peptide variant, wherein said lycotoxin-1 peptide comprises SEQ ID NO: 1, and said variant comprises a proline at amino acid position 24 and a tryptophan at amino acid position 25, and an enterokinase K recognition site, DDDK, at the N-terminus of said lycotoxin-1 peptide.

14. A nucleic acid construct comprising said nucleic acid molecule of claim 7 encoding said lycotoxin-1 peptide variant, wherein said nucleic acid molecule is operably linked to one or more expression control sequences.

15. A host cell transformed with the nucleic acid construct of claim 14.

16. The host cell of claim 15 wherein said cell is *Saccharomyces cerevisiae*.

17. A nucleic acid construct comprising said nucleic acid molecule of claim 13 operably linked to one or more expression control sequences.

18. A host cell transformed with said nucleic acid construct of claim 17.

19. The host cell of claim 18 wherein said cell is *Saccharomyces cerevisiae*.

* * * * *

SEQUENCE LISTING

<160> NUMBER OF SEQ ID NOS: 14

<210> SEQ ID NO 1
<211> LENGTH: 25
<212> TYPE: PRT
<213> ORGANISM: Lycosa carolinensis

<400> SEQUENCE: 1

Ile Trp Leu Thr Ala Leu Lys Phe Leu Gly Lys His Ala Ala Lys His
1               5                   10                  15

Leu Ala Lys Gln Gln Leu Ser Lys Leu
            20                  25

<210> SEQ ID NO 2
<211> LENGTH: 25
<212> TYPE: PRT
<213> ORGANISM: Artificial Sequence
<220> FEATURE:
<223> OTHER INFORMATION: Completely synthesized from synthetic
      oligonucleotides

<400> SEQUENCE: 2

Ile Trp Leu Thr Ala Leu Lys Phe Leu Gly Lys His Ala Ala Lys His
1               5                   10                  15

Leu Ala Lys Gln Gln Leu Ser Pro Trp
            20                  25

<210> SEQ ID NO 3
<211> LENGTH: 25
<212> TYPE: PRT
<213> ORGANISM: Artificial Sequence
<220> FEATURE:
<223> OTHER INFORMATION: Completely synthesized from synthetic
      oligonucleotides

<400> SEQUENCE: 3

Ile Trp Leu Thr Ala Leu Lys His Leu Gly Lys His Ala Ala Lys His
1               5                   10                  15

Leu Ala Lys Gln Gln Leu Ser Pro Trp
            20                  25

<210> SEQ ID NO 4
<211> LENGTH: 25
<212> TYPE: PRT

```
<213> ORGANISM: Artificial Sequence
<220> FEATURE:
<223> OTHER INFORMATION: Completely synthesized from synthetic
      oligonucleotides

<400> SEQUENCE: 4

Ile Trp Leu Thr Ala Leu Lys Phe Leu Gln Lys His Ala Ala Lys His
1               5                   10                  15

Leu Ala Lys Gln Gln Leu Ser Pro Trp
            20                  25

<210> SEQ ID NO 5
<211> LENGTH: 25
<212> TYPE: PRT
<213> ORGANISM: Artificial Sequence
<220> FEATURE:
<223> OTHER INFORMATION: Completely synthesized from synthetic
      oligonucleotides

<400> SEQUENCE: 5

Ile Trp Leu Thr Ala Leu Lys Phe Ser Gly Lys His Ala Ala Lys His
1               5                   10                  15

Leu Ala Lys Gln Gln Leu Ser Pro Trp
            20                  25

<210> SEQ ID NO 6
<211> LENGTH: 25
<212> TYPE: PRT
<213> ORGANISM: Artificial Sequence
<220> FEATURE:
<223> OTHER INFORMATION: Completely synthesized from synthetic
      oligonucleotides

<400> SEQUENCE: 6

Ile Trp Leu Thr Ala Leu Lys Phe Leu Gln Lys His Ala Ala Lys His
1               5                   10                  15

Leu Ala Lys His Ser Leu Ser Pro Trp
            20                  25

<210> SEQ ID NO 7
<211> LENGTH: 29
<212> TYPE: PRT
<213> ORGANISM: Artificial Sequence
<220> FEATURE:
<223> OTHER INFORMATION: Completely synthesized from synthetic
      oligonucleotides

<400> SEQUENCE: 7

Asp Asp Asp Lys Ile Trp Leu Thr Ala Leu Lys Phe Leu Gly Lys His
1               5                   10                  15

Ala Ala Lys His Leu Ala Lys Gln Gln Leu Ser Pro Trp
            20                  25

<210> SEQ ID NO 8
<211> LENGTH: 109
<212> TYPE: DNA
<213> ORGANISM: Artificial Sequence
<220> FEATURE:
<223> OTHER INFORMATION: Completely synthesized from synthetic
      oligonucleotides

<400> SEQUENCE: 8
cacccatcat catcatcatc atgatgatga taaaatctgg ctgaccgcgc tgaaatttct        60
gggcaaacat gcggcgaaac atctggcgaa acagcagttg tcgccatgg                    109
```

-continued

```
<210> SEQ ID NO 9
<211> LENGTH: 109
<212> TYPE: DNA
<213> ORGANISM: Artificial Sequence
<220> FEATURE:
<223> OTHER INFORMATION: Completely synthesized from synthetic
      oligonucleotides

<400> SEQUENCE: 9
cacccatcat catcatcatc atgatgatga taaaatctgg ctgaccgcgc tgaaacacct      60
gggcaaacat gcggcgaaac atctggcgaa acagcagttg tcgccatgg               109

<210> SEQ ID NO 10
<211> LENGTH: 109
<212> TYPE: DNA
<213> ORGANISM: Artificial Sequence
<220> FEATURE:
<223> OTHER INFORMATION: Completely synthesized from synthetic
      oligonucleotides

<400> SEQUENCE: 10
cacccatcat catcatcatc atgatgatga taaaatctgg ctgaccgcgc tgaaatttct      60
gcagaaacat gcggcgaaac atctggcgaa acacagtttg tcgccatgg              109

<210> SEQ ID NO 11
<211> LENGTH: 109
<212> TYPE: DNA
<213> ORGANISM: Artificial Sequence
<220> FEATURE:
<223> OTHER INFORMATION: Completely synthesized from synthetic
      oligonucleotides

<400> SEQUENCE: 11
cacccatcat catcatcatc atgatgatga taaaatctgg ctgaccgcgc tgaaatttag      60
tggcaaacat gcggcgaaac atctggcgaa acagcagttg tcgccatgg              109

<210> SEQ ID NO 12
<211> LENGTH: 35
<212> TYPE: DNA
<213> ORGANISM: Artificial Sequence
<220> FEATURE:
<223> OTHER INFORMATION: Completely synthesized

<400> SEQUENCE: 12
cgcgagctag ccgcgcgttt cggtgatgac ggtga                              35

<210> SEQ ID NO 13
<211> LENGTH: 35
<212> TYPE: DNA
<213> ORGANISM: Artificial Sequence
<220> FEATURE:
<223> OTHER INFORMATION: Completely synthesized

<400> SEQUENCE: 13
cgcgacgcgt gatcggcaag tgcacaaaca atact                              35

<210> SEQ ID NO 14
<211> LENGTH: 35
<212> TYPE: PRT
<213> ORGANISM: Artificial Sequence
<220> FEATURE:
<223> OTHER INFORMATION: Completely synthesized from synthetic
      oligonucleotides

<400> SEQUENCE: 14

His His His His His His Asp Asp Asp Lys Ile Trp Leu Thr Ala Leu
```

```
                 1               5                  10                 15
              Lys Phe Leu Gly Lys His Ala Ala Lys His Leu Ala Lys Gln Gln Leu
                           20                  25                 30

Ser Pro Trp
                      35
```